(12) United States Patent
Abuzaina

(10) Patent No.: US 9,226,811 B2
(45) Date of Patent: Jan. 5, 2016

(54) HERNIA REPAIR SYSTEM

(75) Inventor: Ferass Abuzaina, Shelton, CT (US)

(73) Assignee: Covidien LP, Mansfield, MA (US)

( * ) Notice: Subject to any disclaimer, the term of this patent is extended or adjusted under 35 U.S.C. 154(b) by 134 days.

(21) Appl. No.: 13/981,098

(22) PCT Filed: Feb. 16, 2012

(86) PCT No.: PCT/US2012/025398
§ 371 (c)(1),
(2), (4) Date: Aug. 23, 2013

(87) PCT Pub. No.: WO2012/112752
PCT Pub. Date: Aug. 23, 2012

(65) Prior Publication Data
US 2013/0338687 A1 Dec. 19, 2013

Related U.S. Application Data

(60) Provisional application No. 61/443,402, filed on Feb. 16, 2011.

(51) Int. Cl.
*A61F 2/02* (2006.01)
*A61F 2/00* (2006.01)

(52) U.S. Cl.
CPC ....... *A61F 2/0063* (2013.01); *A61F 2002/0072* (2013.01); *A61F 2250/0031* (2013.01)

(58) Field of Classification Search
CPC ................ A61F 2/0063; A61F 2/0077; A61F 2002/0068
USPC ..................... 606/151, 213; 623/23.72, 23.74
See application file for complete search history.

(56) References Cited

U.S. PATENT DOCUMENTS

| | | | |
|---|---|---|---|
| 5,258,000 A * | 11/1993 | Gianturco | 606/151 |
| 5,366,460 A | 11/1994 | Eberbach | |
| 5,743,917 A * | 4/1998 | Saxon | 128/898 |
| 2003/0130745 A1* | 7/2003 | Cherok et al. | 623/23.72 |
| 2006/0282105 A1* | 12/2006 | Ford et al. | 606/151 |
| 2009/0270999 A1* | 10/2009 | Brown | 623/23.72 |
| 2009/0326676 A1 | 12/2009 | Dupic et al. | |
| 2010/0241145 A1 | 9/2010 | Cook | |
| 2011/0015477 A1* | 1/2011 | Montpetit et al. | 600/37 |
| 2011/0178538 A1 | 7/2011 | Cook | |

OTHER PUBLICATIONS

International Search Report for PCT/US12/25398 date of completion is Jun. 5, 2012 (3 pages).

* cited by examiner

*Primary Examiner* — Todd E Manahan
*Assistant Examiner* — Erich Herbermann

(57) ABSTRACT

A hernia repair system includes a surgical patch, a dispenser, and a plurality of sutures. The surgical patch is movable between a contracted orientation and an expanded orientation. The dispenser includes a housing and a plunger. The housing defines a lumen. The plunger is movably secured within the lumen. The housing is configured to releasably retain the surgical patch within the lumen in the contracted orientation of the surgical patch. The plunger is configured to expel the surgical patch from the housing upon the selective actuation of the plunger from a first position to a second position. The surgical patch is autonomously positionable in the expanded orientation upon being expelled from the lumen. The plurality of sutures are configured to securely mount the surgical patch to a tissue site when the surgical patch is positioned in the expanded orientation.

20 Claims, 4 Drawing Sheets

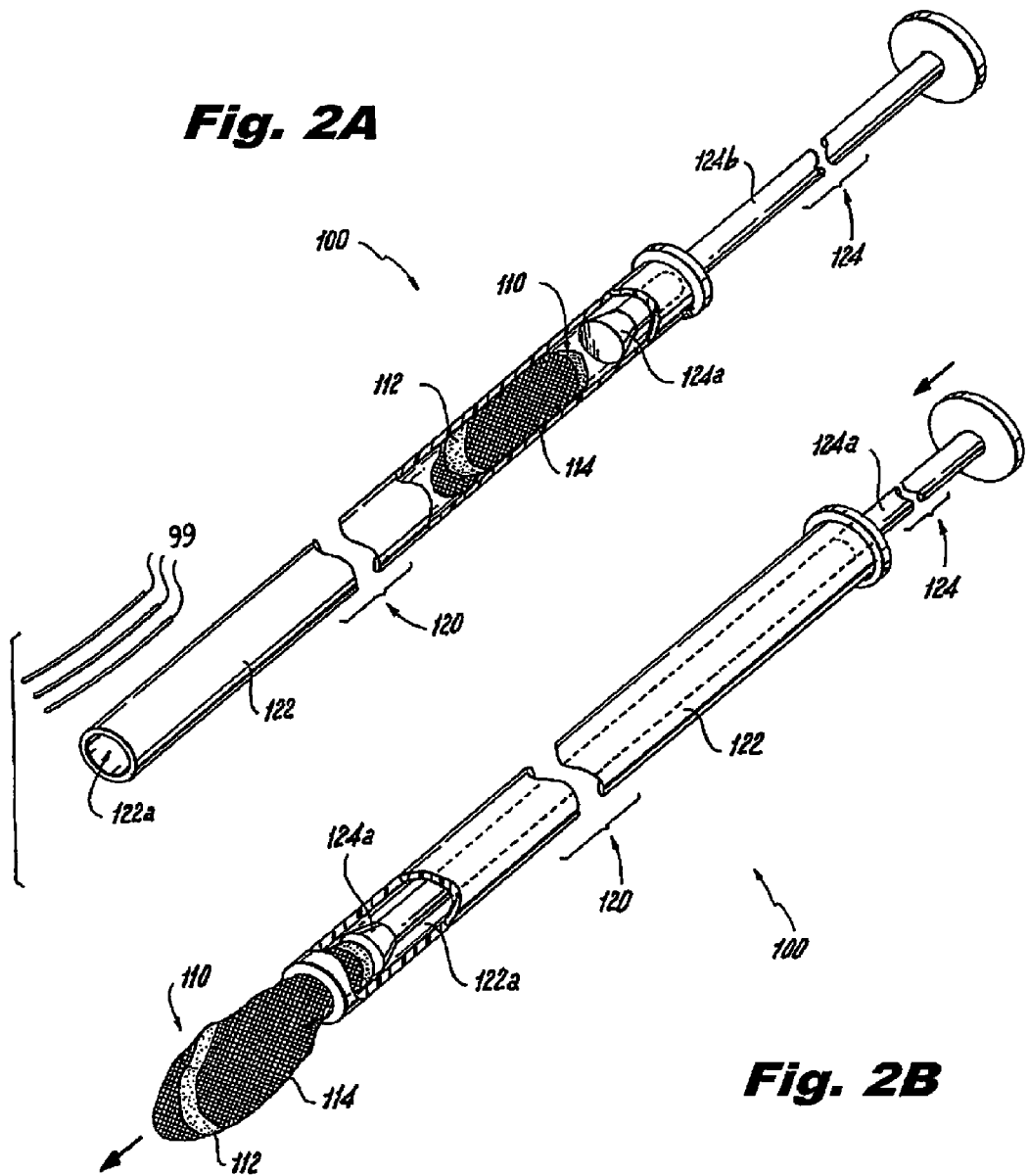

HERNIA REPAIR SYSTEM

CROSS-REFERENCE TO RELATED APPLICATIONS

This application is a National Stage Application of PCT/US12/25398 under 35USC §371 (a), which claims priority of U.S. Provisional Patent Application Ser. No. 61/443,402 filed Feb. 16, 2011, the disclosures of each of the above-identified applications are hereby incorporated by reference in their entirety.

BACKGROUND

1. Technical Field

The present disclosure relates to methods and systems for the application of a surgical patch. More particularly, the present disclosure relates to systems and methods for the deployment and securement of a surgical patch to a tissue site of a hernia.

2. Description of Related Art

A hernia is a protrusion of a tissue, structure, or part of an organ through injured muscle tissue or an injured membrane by which the tissue, structure, or organ is normally contained. Some examples of hernias include: abdominal hernias, diaphragmatic hernias and hiatal hernias (for example, para-esophageal hernia of the stomach), pelvic hernias, for example, obturator hernia, anal hernias, hernias of the nucleus pulposus of the intervertebral discs, intracranial hernias, and Spigelian hernias.

Hernias may be surgically repaired, and are principally repaired by pushing back, or "reducing", the herniated tissue, and then reinforcing the defect in injured muscle tissue (an operation called herniorrhaphy). Modern muscle reinforcement techniques involve placement of a surgical patch, such as a surgical mesh, near the injured tissue or defect to support the defect. The surgical patch is either placed over the defect (anterior repair) or under the defect (posterior repair).

A variety of different fixation devices are used to anchor the surgical patch to the tissue. For example, a needled suture may be passed through or around the tissue near the defect to hold the surgical patch in a position which spans the injured tissue. In other examples, staples, tacks, clips and pins are also known to be passed through or around the tissue near the defect to anchor the surgical patch in a position which spans the injured tissue. Although such methods have been proven effective in anchoring the surgical patch to the tissue, these surgical patches have a tendency to crumble and kink when being positioned or anchored relative to the tissue. Indeed, these surgical patches are most effective when they maintain a snug and flat fit against the tissue. Thus, the crumbling and kinking of the surgical patches may limit the effectiveness of the surgical patches. In this respect, a continuing need still exits to provide a means for facilitating the effectiveness of surgical patches used to surgically repair hernias.

SUMMARY

Accordingly, a hernia repair system includes a surgical patch, a dispenser, and a plurality of sutures. The surgical patch is movable between a contracted orientation and an expanded orientation. The dispenser includes a housing and a plunger. The housing defines a lumen. The plunger is movably secured within the lumen. The housing is configured to releasably retain the surgical patch within the lumen in the contracted orientation of the surgical patch. The surgical patch is folded in the contracted orientation to fit within the lumen of the dispenser housing. The plunger is configured to expel the surgical patch from the housing upon the selective actuation of the plunger from a first position to a second position. The plunger is configured to engage the surgical patch so as to apply a pulling force on the surgical patch after deployment of the surgical patch from the housing. The pulling force is sufficient to ensure the securement of the surgical patch to a tissue site. The surgical patch is autonomously positionable in the expanded orientation upon being expelled from the lumen. The plurality of sutures is configured to securely mount the surgical patch to the tissue site when the surgical patch is positioned in the expanded orientation.

In the expanded orientation, the surgical patch is configured to remain substantially flush with the tissue site and may be substantially planar. The surgical patch includes a stiffening portion configured to unfold the surgical patch into the expanded orientation. The stiffening portion may be annular. The stiffening portion may be absorbable.

According to one embodiment, the surgical patch includes a sleeve extending therefrom for facilitating a temporary fixation of the surgical patch to the tissue site. The sleeve includes a plurality of gripping features configured to adhere to tissue. In some embodiments, the surgical patch includes one or more tethers extending therefrom. The one or more tethers are configured to facilitate the fixation of the surgical patch to the tissue site.

According to one aspect, a hernia repair method includes providing a hernia repair system including a surgical patch, a dispenser, and a plurality of sutures. The method involves dispensing the surgical patch from the dispenser so that the surgical patch autonomously transitions from a contracted condition to an expanded condition upon being dispensed from the dispenser, positioning the surgical patch at a tissue site in the expanded condition, and positioning two or more sutures about the surgical patch via a mattress suture technique to facilitate the distribution of tension through the surgical patch and to keep the surgical patch positioned flat against the tissue site.

BRIEF DESCRIPTION OF THE DRAWINGS

The above and other aspects, features, and advantages of the present disclosure will become more apparent in light of the following detailed description when taken in conjunction with the accompanying drawings in which:

FIGS. 2A-2D are progressive views illustrating the deployment of one embodiment of the presently disclosed surgical patch from the dispenser of the presently disclosed hernia repair system;

DETAILED DESCRIPTION

Figure 1A:
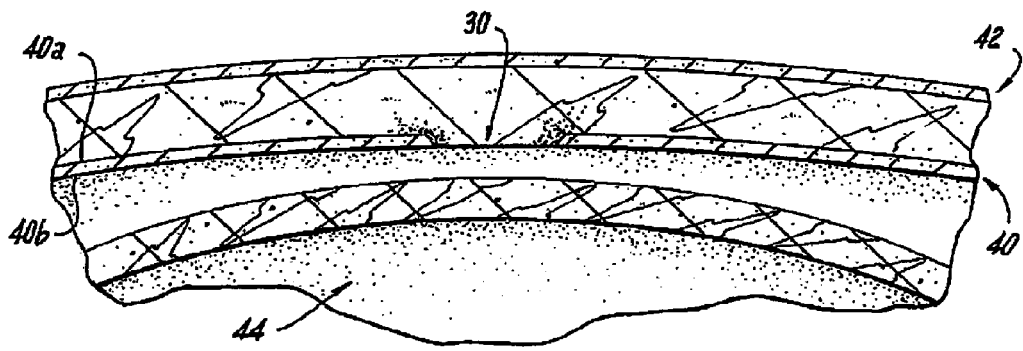
FIG. 1A is a cross-sectional view illustrating a tear in an abdominal wall.

The present disclosure relates to devices, systems, and methods for surgeries such as transluminal and/or endoluminal placement of a surgical patch at a surgical site. As used herein the term "surgical patch" is used to refer to any type of patch for use in surgical procedures, such as, for example, meshes that can be attached to the abdominal wall. Although described herein with reference to a hernia surgical patch, the methods of the disclosure may be used in any surgical repair.

In the drawings and in the description that follows, the term "proximal," as is traditional, will refer to an end of a device that is closer to the user, while the term "distal" will refer to the end of the device that is farther from the user.

Figure 1B:
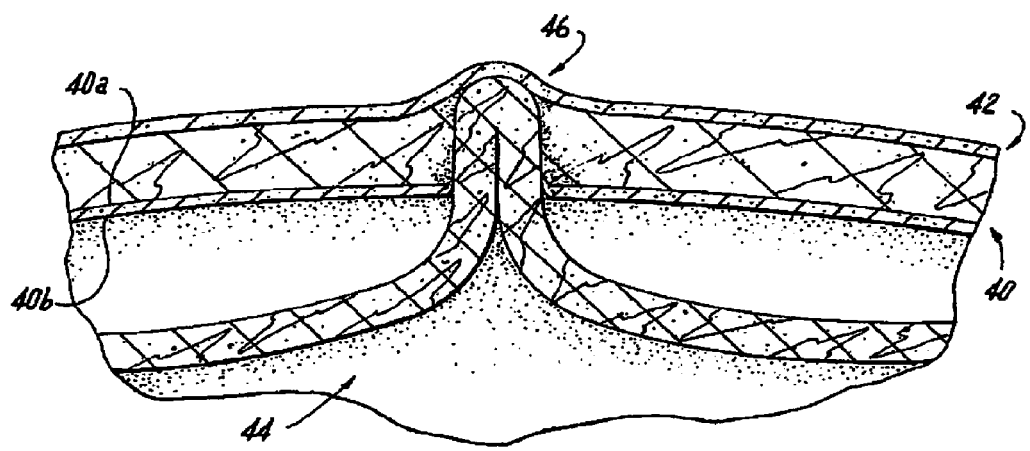
FIG. 1B is a cross-sectional view illustrating a ventral hernia.

Referring now in specific detail to the drawings, in which like numbers identify similar or identical elements, FIG. 1A illustrates a hernia that may involve a tear 30 in the abdominal wall 40. The abdominal wall 40 is defined by an external side 40a and an internal side 40b. A surface tissue 42, which covers the external side 40a of abdominal wall 40, may or may not be immediately affected by this tear 30. An internal organ 44 located below the internal side 40b of the abdominal wall 40 may not protrude until some form of exertion or use of the muscle located at the abdominal wall 40 forces the internal organ 44 into the tear 30. Depending on the size and location of the tear 30, exertion may not be needed to cause the organ to protrude. As shown in FIG. 1B, a hernia occurs when an internal organ 44 protrudes into the tear 30 of abdominal wall 40. Oftentimes the protrusion creates a bulge 46 in the surface tissue 42.

Figure 2C:
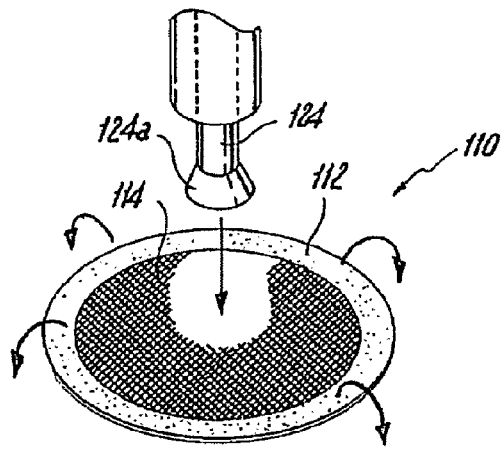
Figure 2D:
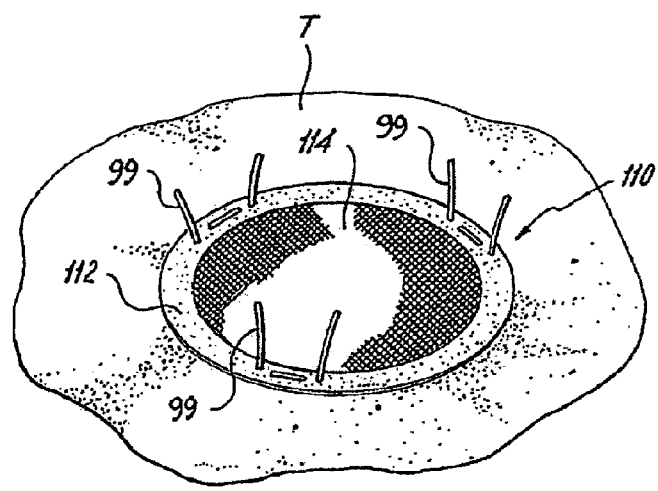

As depicted in FIGS. 2A-2D, a hernia repair system 100 includes a surgical patch 110, a dispenser 120, and a plurality of sutures 99. The dispenser 120 includes a housing 122 and a plunger 124. The housing 122 defines a lumen 122a within which the plunger 124 is movably secured. The plunger 124 includes a shaft 124b and a head 124a at the distal end of the shaft 124b. The surgical patch 110 is positionable within the housing 122 in a contracted orientation such that the housing 122 releasably retains the surgical patch 110. As described in greater detail below, the surgical patch 110 can be rolled, folded or oriented in any suitable manner in order to maintain a contracted orientation whereby the surgical patch 110 securely fits within the housing 122. As best illustrated in FIG. 2A, the surgical patch 110 may folded in the contracted orientation to fit within the lumen 122a of the dispenser housing 122 in a releasably secured condition.

In use, from FIG. 2B, the plunger 124 expels the surgical patch 110 from the distal end of the lumen 122a of the housing 122 upon the selective actuation of the plunger 124. In particular, the plunger 124 is moved from a first position, where the plunger 124 is positioned in a proximal portion of the lumen 122a adjacent the surgical patch 110 such that the head 124a of the plunger 124 may be in contacting relation with the surgical patch 110, to a second position, where the head 124a of the plunger 124, via the shaft 124b of the plunger 124, is advanced to the distal end of the lumen 122a, dispensing the surgical patch 110 from the distal end of the housing 122, which is an open end. In this respect, there is relative movement between the plunger 124 and the housing 122 to expel the surgical patch 110. Upon being expelled from the lumen 122a of the housing 122 via the open distal end, the surgical patch 110 is autonomously positionable in an expanded orientation. More particularly, the surgical patch 110, which includes a stiffening portion 112 and a central portion 114, unfolds into the expanded orientation by virtue of the stiffening portion 112, transitioning itself into a fully extended state. In this manner, the stiffening portion 112 is biased towards the extended state, but transitions to the extended state from a contracted state when tension is removed. The stiffening portion 112 may be annular and encircle the central portion 114. As such, the stiffening portion 112 pulls the central portion 114 into a flat and/or planar orientation. As described in greater detail below, the stiffening portion 112 and/or the central portion 114 may be absorbable.

After deployment of the surgical patch 110, the plunger 124 is configured to engage the surgical patch 110 so as to apply a pulling force on the surgical patch 110. The pulling force is sufficient to ensure the securement of the surgical patch 110 to a tissue site "T." In the expanded orientation, the surgical patch 110 is configured to remain substantially flush with the tissue site "T" whereby the surgical patch is substantially free from kinking, crumpling, bunching, and/or folding. However, the aid of the pulling force applied by the plunger 124 further facilitates the flush positioning of the surgical patch 110 relative to the tissue site "T" by pulling the surgical patch 110 into a taut condition to substantially eliminate any undesirable kinking, crumpling, bunching and/or folding. After the surgical patch 110 is positioned relative to the tissue site "T", the sutures 99 are utilized to securely mount the surgical patch 110 to the tissue site "T."

Figure 3:
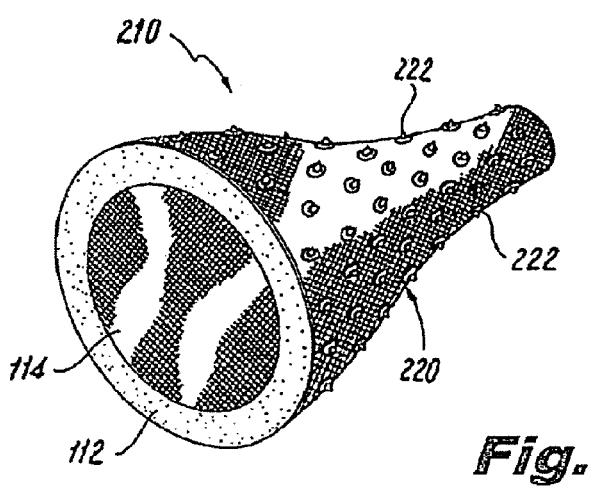
FIG. 3 is a top view of another embodiment of the presently disclosed surgical patch.

With reference to FIG. 3, one embodiment of the presently disclosed surgical patch is generally referred to as surgical patch 210. Surgical patch 210 is similar to surgical patch 110 and is described herein only to the extent necessary to describe the differences in construction and operation relative to surgical patch 110. Surgical patch 210 includes a sleeve 220 extending therefrom for facilitating a temporary fixation of the surgical patch 210 to the tissue site "T." The sleeve 220 includes a plurality of gripping features 222 configured to adhere to tissue after the surgical patch 210 is positioned at the tissue site "T." Examples of these gripping features 222, which can be described as spiked naps, are disclosed in U.S. Pat. No. 7,331,199, the entire contents of which are incorporated herein by this reference.

Figure 4:
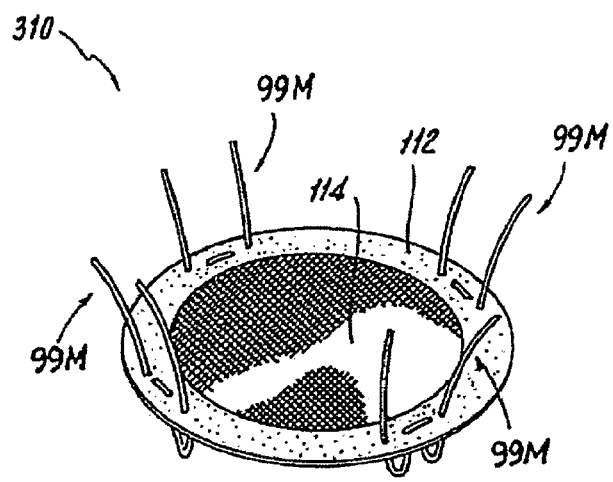
FIG. 4 is a top view of yet another embodiment of the presently disclosed surgical patch.

Referring now to FIG. 4, another embodiment of the presently disclosed surgical patch is generally referred to as surgical patch 310. Surgical patch 310 is similar to surgical patch 110 and is described herein only to the extent necessary to describe the differences in construction and operation relative to surgical patch 110. Surgical patch 310 includes one or more mattress sutures 99M. In this manner, the surgical patch 310 may be mounted to tissue with one or more sutures via any suitable mattress suture technique known in the art including, but not limited to, vertical, horizontal, and corner stitching. As illustrated, two or more mattress sutures 99M are positionable about the surgical patch 310 to facilitate the distribution of tension through the surgical patch 310 and to keep the surgical patch 310 positioned flat/flush against the tissue site "T."

Figure 5:
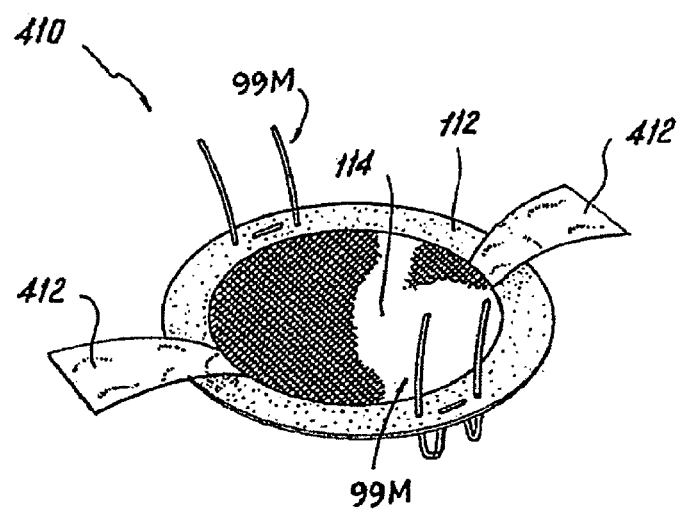
FIG. 5 is a top view of another embodiment of the presently disclosed surgical patch.

Referring now to FIG. 5, another embodiment of the presently disclosed surgical patch is generally referred to as surgical patch 410. Surgical patch 410 is similar to surgical patch 310 and is described herein only to the extent necessary to describe the differences in construction and operation relative to surgical patch 310. Surgical patch 410 includes one or more tethers 412 extending therefrom. The one or more tethers 412 are configured to facilitate the fixation of the surgical patch 410 to the tissue site "T." Similar to surgical patch 310, surgical patch 410 may include one or more mattress sutures 99M.

The presently disclosed surgical patch may be any type of patch for use in surgical repair and suitable for use in situ. The surgical patch may be any suitable shape (i.e., circular, non-circular, etc.) and may include one or more layers. The surgical patch may be made of multiple fibers, or may be made of a single fiber. The fibers may be a monofilament or multifilament.

The fibers forming the presently disclosed patch may be made from a natural material or a synthetic material. The fibers may be biodegradable or non-biodegradable. Any combination of natural, synthetic, bioadegradable and non-biodegradable materials may be used to form the fibers. The term "biodegradable" as used herein is defined to include both bioabsorbable and bioresorbable materials. By biodegradable, it is meant that the materials decompose, or lose structural integrity under body conditions (e.g. enzymatic degradation or hydrolysis) or are broken down (physically or chemically) under physiologic conditions in the body such that the degradation products are excretable or absorbable by the body.

Representative natural biodegradable polymers include: polysaccharides, such as alginate, dextran, chitin, hyaluronic acid, cellulose, collagen, gelatin, fucans, glycosaminoglycans, and chemical derivatives thereof (substitutions and/or additions of chemical groups, for example, alkyl, alkylene, hydroxylations, oxidations, and other modifications routinely made by those skilled in the art); and proteins, such as albumin, casein, zein, silk, and copolymers and blends thereof, alone or in combination with synthetic polymers.

Synthetically modified natural polymers include cellulose derivatives, such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, and cellulose sulfate sodium salt. These are collectively referred to herein as "celluloses."

Representative synthetic degradable polymers include polyhydroxy acids prepared from lactone monomers, such as glycolide, lactide, caprolactone, ε-caprolactone, valerolactone, and δ-valerolactone, as well as pluronics, carbonates (e.g., trimethylene carbonate, tetramethylene carbonate, and the like), dioxanones (e.g., 1,4-dioxanone and ε-dioxanone), 1,dioxepanones (e.g., 1,4-dioxepan-2-one and 1,5-dioxepan-2-one), and combinations thereof. Polymers formed therefrom include: polylactides; poly(lactic acid); polyglycolides; poly(glycolic acid); poly(trimethylene carbonate); poly(dioxanone); poly(hydroxybutyric acid); poly(hydroxyvaleric acid); poly(lactide-co-(ε-caprolactone-)); poly(glycolide-co-(ε-caprolactone)); polycarbonates; poly(pseudo amino acids); poly(amino acids); poly(hydroxyalkanoate)s; polyalkylene oxalates; polyoxaesters; polyanhydrides; polyortho esters; and copolymers, block copolymers, homopolymers, blends, and combinations thereof.

Some non-limiting examples of suitable non-bioabsorbable materials from which the fibers may be made include: polyolefins, such as polyethylene and polypropylene including atactic, isotactic, syndiotactic, and blends thereof; polyethylene glycols; polyethylene oxides; ultra high molecular weight polyethylene; copolymers of polyethylene and polypropylene; polyisobutylene and ethylene-alpha olefin copolymers; fluorinated polyolefins, such as fluoroethylenes, fluoropropylenes, fluoroPEGSs, and polytetrafluoroethylene; polyamides, such as nylon and polycaprolactam; polyamines; polyimines; polyesters, such as polyethylene terephthalate and polybutylene terephthalate; aliphatic polyesters; polyethers; polyether-esters, such as polybutester; polytetramethylene ether glycol; 1,4-butanediol; polyurethanes; acrylic polymers and copolymers; modacrylics; vinyl halide polymers and copolymers, such as polyvinyl chloride; polyvinyl alcohols; polyvinyl ethers, such as polyvinyl methyl ether; polyvinylidene halides, such as polyvinylidene fluoride and polyvinylidene chloride; polyacrylonitrile; polyaryletherketones; polyvinyl ketones; polyvinyl aromatics, such as polystyrene; polyvinyl esters, such as polyvinyl acetate; copolymers of vinyl monomers with each other and olefins, such as etheylene-methyl methacrylate copolymers, acrylonitrile-styrene copolymers, ABS resins, and ethylene-vinyl acetate copolymers; alkyd resins; polycarbonates; polyoxymethylenes; polyphosphazine; polyimides; epoxy resins; aramids, rayon; rayon-triacetate; spandex; silicones; and combinations thereof.

The surgical patch of the present disclosure may be formed using any method suitable to forming patch structures, including but not limited to knitting, weaving, non-woven techniques, and the like. Suitable techniques for making the surgical patch are within the purview of those skilled in the art.

The surgical patch may be any shape or size suitable for covering the herniated area and securing the patch to surrounding tissue. The surgical patch may be preformed to a certain size, such as, for example, a 9 cm diameter round patch or 50 cm×50 cm square patch. In embodiments, the surgical patch may be cut to a particular size and shape as needed.

The presently disclosed surgical patch may include a bioactive agent. The term "bioactive agent", as used herein, is used in its broadest sense and includes any substance or mixture of substances that have clinical use. Consequently, bioactive agents may or may not have pharmacological activity per se, e.g., a dye. Alternatively a bioactive agent could be any agent that provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. The bioactive agent may be applied to the surgical patch in any suitable form, e.g., films, powders, liquids, gels, and the like.

Examples of classes of bioactive agents, which may be utilized in accordance with the present disclosure include: anti-adhesives; antimicrobials; analgesics; antipyretics; anesthetics; antiepileptics; antihistamines; anti-inflammatories; cardiovascular drugs; diagnostic agents; sympathomimetics; cholinomimetics; antimuscarinics; antispasmodics; hormones; growth factors; muscle relaxants; adrenergic neuron blockers; antineoplastics; immunogenic agents; immunosuppressants; gastrointestinal drugs; diuretics; steroids; lipids; lipopolysaccharides; polysaccharides; platelet activating drugs; clotting factors; and enzymes. It is also intended that combinations of bioactive agents may be used.

Anti-adhesive agents can be used to prevent adhesions from forming between the patch and the surrounding tissues opposite the target tissue. In addition, anti-adhesive agents may be used to prevent adhesions from forming between the coated implantable medical device and the packaging material. Some examples of these agents include, but are not limited to hydrophilic polymers such as poly(vinyl pyrrolidone), carboxymethyl cellulose, hyaluronic acid, polyethylene oxide, poly vinyl alcohols, and combinations thereof.

Suitable antimicrobial agents which may be included as a bioactive agent include: triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine; polymyxin, tetracycline; aminoglycosides, such as tobramycin and gentamicin; rifampicin; bacitracin; neomycin; chloramphenicol; miconazole; quinolones such as oxolinic acid, norfloxacin, nalidixic acid, pefloxacin, enoxacin and ciprofloxacin; penicillins such as oxacillin and pipracil, nonoxynol 9, fusidic acid, cephalosporins; and combinations thereof. In addition, antimicrobial proteins and peptides such as bovine lactoferrin and lactoferricin B may be included as a bioactive agent.

Other bioactive agents, which may be included as a bioactive agent include local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents, such as coronary vasodilators and nitroglycerin; alkaloids; analgesics; narcotics such as codeine, dihydrocodeinone, meperidine, morphine and the like; nonnarcotics, such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents, such as hormonal agents, hydrocortisone, prednisolone, prednisone, non-hormonal agents, allopurinol, indomethacin, phenylbutazone and the like; prostaglandins and cytotoxic drugs; chemotherapeutics, estrogens; antibacterials; antibiotics; anti-fungals; anti-virals; anticoagulants; anticonvulsants; antidepressants; antihistamines; and immunological agents.

Other examples of suitable bioactive agents, which may be included in the presently disclosed surgical patch include: viruses and cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (IL-2, IL-3, IL-4, IL-6); interferons (β-IFN, α-IFN and γ-IFN); erythropoietin; nucleases; tumor necrosis factor; colony stimulating factors (e.g., GCSF, GM-CSF, MCSF); insulin; anti-tumor agents and tumor suppressors; blood proteins such as fibrin, thrombin, fibrinogen, synthetic thrombin, synthetic fibrin, synthetic fibrinogen; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); bone morphogenic proteins; TGF-B; protein inhibitors; protein antagonists; protein agonists; nucleic acids, such as antisense molecules, DNA, RNA, RNAi; oligonucleotides; polynucleotides; and ribozymes.

In addition, the surgical patch of the present disclosure may be rolled, folded, or otherwise oriented so that the surgical patch forms a shape more appropriate for transfer through the dispenser 120.

In any of the above embodiments of the presently disclosed surgical patch, the surgical patch may include a stiffening portion configured to unfold the surgical patch into the expanded orientation; the stiffening portion may be annular and/or absorbable. Any embodiments of the surgical patch may include a sleeve extending therefrom for facilitating a temporary fixation of the surgical patch to the tissue site; the sleeve may include a plurality of gripping features configured to adhere to tissue. Any embodiments of the surgical patch may include one or more tethers extending therefrom; the one or more tethers are configured to facilitate the fixation of the surgical patch to the tissue site. Furthermore, any number of sutures may be positioned about any of the embodiments of the surgical patch via any suitable mattress suture technique to facilitate the distribution of tension through the surgical patch.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A hernia repair system, comprising:
a surgical patch movable between a contracted orientation and an expanded orientation, the surgical patch including a plurality of sutures positioned within a stiffening layer of the surgical patch; and
a dispenser including a housing and a plunger, the housing defining a lumen, the plunger being movably secured within the lumen, the housing configured to releasably retain the surgical patch within the lumen in the contracted orientation of the surgical patch, the plunger configured to expel the surgical patch from the housing upon the selective actuation of the plunger from a first position to a second position; and
wherein the stiffening layer is configured to autonomously position the surgical patch into the expanded orientation upon being expelled from the dispenser, and the plurality of sutures is configured to securely mount the surgical patch to a tissue site when the surgical patch is positioned in the expanded orientation.

2. The hernia repair system of claim 1, wherein in the expanded orientation, the surgical patch is configured to remain substantially flush with the tissue site.

3. The hernia repair system of claim 1, wherein in the expanded orientation, the surgical patch is planar.

4. The hernia repair system of claim 1, wherein in the contracted orientation, the surgical patch is folded to fit within the lumen of the dispenser housing.

5. The hernia repair system of claim 1, wherein the stiffening layer is annular.

6. The hernia repair system of claim 1, wherein the stiffening layer is absorbable.

7. The hernia repair system of claim 1, wherein the surgical patch includes a sleeve extending therefrom for facilitating a temporary fixation of the surgical patch to the tissue site, the sleeve including a plurality of gripping features configured to adhere to tissue.

8. The hernia repair system of claim 1, wherein the surgical patch includes at least one tether extending therefrom, the at least one tether configured to facilitate the fixation of the surgical patch to the tissue site.

9. The hernia repair system of claim 8, wherein the surgical patch further includes a central portion encircled by the stiffening layer.

10. The hernia repair system of claim 9, wherein the at least one tether is positioned between the central portion and the stiffening layer of the surgical patch.

11. The hernia repair system of claim 1, wherein the plunger is configured to engage the surgical patch so as to apply a pulling force on the surgical patch after deployment of the surgical patch from the housing, the pulling force being sufficient to ensure the securement of the surgical patch to the tissue site.

12. The hernia repair system of claim 1, wherein the plurality of sutures includes at least one mattress suture.

13. The hernia repair system of claim 1, wherein the stiffening layer is formed around an outer-most periphery of the surgical patch.

14. The hernia repair system of claim 1, wherein the stiffening layer includes an outer perimeter and an inner perimeter, the inner perimeter surrounding an outer perimeter of a central portion of the surgical patch, the surgical patch including at least one tether disposed between the inner perimeter of the stiffening layer and the outer perimeter of the central portion.

15. The hernia repair system of claim 14, wherein the at least one tether includes a plurality of tethers, the plurality of tethers and the plurality of sutures alternating with one another radially about the outer perimeter of the central portion of the surgical patch.

16. A hernia repair method, comprising:
providing a hernia repair system including a surgical patch, a dispenser, and a plurality of sutures, wherein the plurality of sutures are positioned within a stiffening layer of the surgical patch;
dispensing the surgical patch from the dispenser so that the stiffening layer of the surgical patch autonomously transitions the surgical patch from a contracted orientation to an expanded orientation upon being dispensed from the dispenser;
positioning the surgical patch at a tissue site in the expanded orientation; and
mounting the surgical patch to tissue with the plurality of sutures to facilitate the distribution of tension through the surgical patch and to keep the surgical patch positioned flat against the tissue site.

17. The hernia repair method of claim 16, wherein dispensing the surgical patch from the dispenser further comprises actuating a plunger from a first position within a housing of the dispenser to a second position outside the housing thereby expelling the surgical patch from the housing.

18. The hernia repair method of claim 17, further comprising engaging the surgical patch with the plunger following the positioning of the surgical patch at the tissue site, so as to apply a pulling force on the surgical patch, the pulling force sufficient to ensure securement of the surgical patch to the tissue site.

19. The hernia repair method of claim 16, wherein the surgical patch further includes at least one tether extending therefrom, the at least one tether configured to facilitate fixation of the surgical patch to the tissue site.

20. The hernia repair method of claim 16, wherein autonomous transitioning of the surgical patch from the contracted orientation to the expanded orientation includes applying stiffening forces around an outer-most periphery of the surgical patch via the stiffening layer.

* * * * *